US007700806B2

(12) United States Patent
van Cauwenberge et al.

(10) Patent No.: US 7,700,806 B2
(45) Date of Patent: Apr. 20, 2010

(54) METHOD FOR PRODUCING ETHYLENE AMINES ETHANOL AMINES FROM MONOETHYLENE GLYCOL (MEG)

(75) Inventors: Gunther van Cauwenberge, Temse (BE); Johann-Peter Melder, Böhl-Iggelheim (DE); Bram Willem Hoffer, Heidelberg (DE); Thomas Krug, Worms (DE); Karin Pickenäcker, Lampertheim (DE); Frank-Friedrich Pape, Kleinniedesheim (DE); Ekkehard Schwab, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/279,254

(22) PCT Filed: Feb. 5, 2007

(86) PCT No.: PCT/EP2007/051061

§ 371 (c)(1),
(2), (4) Date: Aug. 13, 2008

(87) PCT Pub. No.: WO2007/093514

PCT Pub. Date: Aug. 23, 2007

(65) Prior Publication Data
US 2009/0240084 A1 Sep. 24, 2009

(30) Foreign Application Priority Data
Feb. 14, 2006 (EP) .................... 06101643

(51) Int. Cl.
C07C 209/16 (2006.01)
(52) U.S. Cl. .................................. 564/480
(58) Field of Classification Search .......... None
See application file for complete search history.

(56) References Cited

U.S. PATENT DOCUMENTS

| 4,014,933 | A | 3/1977 | Boettger et al. |
| 4,568,746 | A | 2/1986 | Cowherd, III |
| 4,645,834 | A | 2/1987 | Dixon et al. |
| 4,647,663 | A | 3/1987 | Dixon et al. |
| 4,855,505 | A | 8/1989 | Köll |
| 5,002,922 | A | 3/1991 | Irgang et al. |
| 5,410,086 | A | 4/1995 | Burgess |
| 5,958,825 | A | 9/1999 | Wulff-Döring et al. |
| 6,187,957 | B1 | 2/2001 | Meyer et al. |
| 6,525,222 | B2 | 2/2003 | Nouwen et al. |
| 7,393,978 | B2 | 7/2008 | Frauenkron et al. |
| 2005/0107637 | A1 | 5/2005 | Gerlach et al. |
| 2006/0276649 | A1 | 12/2006 | Frauenkron et al. |
| 2007/0043217 | A1 | 2/2007 | Siegert et al. |
| 2007/0100144 | A1 | 5/2007 | Frauenkron et al. |
| 2008/0221359 | A1 | 9/2008 | Gerlach et al. |
| 2008/0255351 | A1 | 10/2008 | Hoffer et al. |
| 2008/0255360 | A1 | 10/2008 | Van Cauwenberge et al. |

FOREIGN PATENT DOCUMENTS

| DE | 1953263 | | 2/1972 |
| DE | 19859776 | A1 | 6/2000 |
| DE | 10349059 | A1 | 5/2005 |
| DE | 102005019373 | A1 | 11/2006 |
| DE | 102005047464 | A1 | 4/2007 |
| EP | 0036331 | A2 | 9/1981 |
| EP | 0382049 | A1 | 8/1990 |
| EP | 0839575 | A2 | 5/1998 |
| EP | 0963975 | A1 | 12/1999 |
| EP | 1106600 | A2 | 6/2001 |
| GB | 1319495 | | 6/1973 |
| GB | 1508460 | | 4/1978 |
| JP | 59115746 | A | 7/1984 |
| WO | WO-96/38226 | A1 | 12/1996 |
| WO | WO-03/010125 | A1 | 2/2003 |
| WO | WO-03/076386 | A2 | 9/2003 |
| WO | WO-2005/012223 | A1 | 2/2005 |
| WO | WO-2005/014523 | A1 | 2/2005 |
| WO | WO-2005/014623 | A2 | 2/2005 |
| WO | WO-2005/061430 | A1 | 7/2005 |
| WO | WO-2006/114417 | A1 | 11/2006 |
| WO | WO-2007/036496 | A1 | 4/2007 |
| WO | WO-2007/036498 | A1 | 4/2007 |
| WO | WO-2007/036499 | A1 | 4/2007 |

OTHER PUBLICATIONS

Kronich, I.G., et al., "Gas-Phase Synthesis of Morpholine from Diethylene Glycol and Ammonia", The Soviet Chemical Industry, 1982, vol. 14, pp. 1318-1330.

(Continued)

Primary Examiner—Brian J Davis
(74) Attorney, Agent, or Firm—Connolly Bove Lodge & Hutz LLP

(57) ABSTRACT

A process for preparing ethylene amines and ethanolamines by hydrogenative amination of monoethylene glycol and ammonia in the presence of a catalyst, wherein the process is carried out in two process stages in which
in the first process stage, the amination is carried out over a hydroamination catalyst to a monoethylene glycol conversion of not more than 40% and
in the second process stage, a supported catalyst having an active composition comprising ruthenium and cobalt and no further additional metal of group VIII and also no metal of group IB is used in the form of shaped catalyst bodies which in the case of a spherical shape or rod shape in each case have a diameter of <3 mm, in the case of a pellet shape have a height of <3 mm and in the case of all other geometries in each case have an equivalent diameter $L=1/a'$ of <0.70 mm, is proposed.

12 Claims, No Drawings

OTHER PUBLICATIONS

Khim. Prom-st. (Moscow), 1982, vol. 11, pp. 653-655.
Zh. Vses. Khim. Obshchest., 1969, vol. 14, No. 5, pp. 589-590.
Catalysis in Kirk othmer Encyclopedia of Chemical Technology Copyright © 2002 by John Wiley & Sons, Inc. pp. 200-254.
Arné, M., "Alkyl Amines", SRI International, 1981, PEP Report No. 138, pp. 7-8, 13-16, 43-107, 113, and 117.
Barnes, C. M., et al., "Ethylenediamine by Low-Pressure Ammonolysis of Monoethanolamine", Ind. Eng. Chem. Prod. Res. Dev., 1981, vol. 20, pp. 399-407.
Kusaka, H., et al., "Characterization and Nitrile Group Hydrogenation Study of Supported and Unsupported Ru-Co Catalyst", Journal of Catalysis, 1996, vol. 161, pp. 96-106.

METHOD FOR PRODUCING ETHYLENE AMINES ETHANOL AMINES FROM MONOETHYLENE GLYCOL (MEG)

RELATED APPLICATIONS

This application is a national stage application (under 35 U.S.C. §371) of PCT/EP2007/051061, filed Feb. 5, 2007, which claims benefit of European application 06101643.2, filed Feb. 14, 2006.

The invention relates to a process for preparing ethylene amines and ethanolamines by hydrogenative amination of monoethylene glycol (hereinafter: MEG) and ammonia in the presence of a catalyst.

In known processes, a mixture of ethanolamines and ethylene amines is generally obtained; among these, ethylenediamine (hereinafter: EDA) and diethylenetriamine (bis(2-aminoethyl)amine; hereinafter: DETA), in particular, are important materials of value, among other things for use as solvents, stabilizers, for the synthesis of chelating agents, synthetic resins, drugs, inhibitors and surface-active substances.

EDA is used, in particular, as raw material for fungicides and insecticides

DETA is used, in particular, as a solvent for dyes and serves as starting material for producing ion exchangers, pesticides, antioxidants, corrosion inhibitors, complexing agents, textile assistants and absorbents for (acidic) gases.

Nonlinear amines in the product mixture of ethylene amines and ethanolamines and in particular cyclic amines, predominantly piperazine and piperazine derivatives, are comparatively less sought after to undesirable.

Numerous methods of preparing ethylene amines are described in the literature.

According to PEP Report No. 138, "Alkyl Amines", SRI International, 03/1981, in particular pages 7, 8, 13-16, 43-107, 113, 117, the reaction of dichloroethane with ammonia at a molar ratio of 1:15 gives DETA with a proportion of the ethylene amines formed of greater than 20% by weight. However, 40% by weight of higher ethylene amines are formed in addition to 40% by weight of EDA.

Amination of monoethanolamine (hereinafter: MEOA) by means of ammonia (cf., for example, the abovementioned PEP Report, U.S. Pat. No. 4,014,933 (BASF AG) enables the formation of these higher ethylene amines (i.e. ethylene amines having a boiling point above that of triethylenetetramine (hereinafter: TETA)) to be largely suppressed in favor of EDA. However, aminoethylethanolamine (hereinafter: AEEA) and piperazine (hereinafter: PIP) are obtained as by-products in this reaction.

Ind. Eng. Chem. Prod. Res. Dev. 1981, 20, pages 399-407 (C. M. Barnes et al.) describes the ammonolysis of MEOA to form EDA over nickel catalysts on a mixed $SiO_2$-$Al_2O_3$ support. Addition of water and the powered catalyst are said to have been advantageous in increasing the yield of EDA.

Disadvantages of these technologies using suspended catalysts result, inter alia, from the catalyst/product separation required. Furthermore, the selectivities, e.g. for the formation of DETA, are in need of improvement.

WO-A-051014623 (BASF AG) relates to a process for preparing ethylene amines (e.g. DETA) by reaction of MEOA with ammonia in the presence of a catalyst in a reactor (1) and fractionation of the resulting reaction product mixture, with EDA obtained in the fractionation being reacted in a separate reactor (2) in the presence of a catalyst to form DETA and the resulting reaction product mixture being fed to the fractionation of the reaction product mixture resulting from reactor 1.

The earlier German patent application No. 102005019373.0 of Apr. 26, 2005 (BASF AG) relates to a process for preparing ethylene amines, in which ethylene oxide is reacted continuously with ammonia over an inorganic ion exchanger under water-free conditions in a first reaction stage, with the resulting reaction product comprising monoethanolamine, diethanolamine and triethanolamine in a particular weight ratio, and the reaction product is subsequently reacted continuously with ammonia in the presence of hydrogen and a hydrogenation catalyst in a second reaction stage.

However, the process has, in particular, the disadvantage that ethylene oxide of high purity has to be used as starting material.

It is known from DE 102005047464.0 that the acyclic amines, in particular EDA and DETA, can be obtained in high yields and selectivities from MEOA by hydrogenative amination from a heterogeneous catalyst comprising compounds of aluminum, copper, nickel and cobalt as used and the shaped catalyst bodies have a geometry corresponding to the following definition:

The shaped catalyst bodies should in the case of a spherical or rod shape have a diameter in each case of <3 mm, in the case of a pellet shape have a height of <3 mm and in the case of all other geometries in each case have an equivalent diameter L=1/a' of <0.70 mm, where a' is the external surface area per unit volume ($mm_s^2/mm_p^3$) and:

$$a' = \frac{Ap}{Vp}$$

where $A_p$ is the external surface area of the catalyst particle ($mm_s^2$) and $V_p$ is the volume of the catalyst particle ($mm_p^3$).

WO 96/38226 discloses catalysts comprising rhenium, nickel, cobalt, boron and copper and/or ruthenium on a support material and having a weight ratio of nickel to rhenium in the range from 1 to 30 and a weight ratio of nickel to cobalt, of nickel to boron and of nickel to copper and/or ruthenium of in each case 1:20. The catalyst is used for the reductive amination of alkanes or arylalkane derivatives, for example by means of ammonia in the presence of hydrogen, in particular of MEOA. Many further alkane derivatives are also mentioned by way of example as starting materials, including ethylene glycol. It cannot be deduced from the document that the catalyst described would in the process step of the conversion of monoethylene glycol into monoethanolamine display an increased selectivity compared to the subsequent reactions of monoethanolamine.

U.S. Pat. No. 4,855,505 discloses a process for the hydroamination of, for example, monoethylene glycol by means of, for example, ammonia in the presence of a catalyst comprising from 4 to 40% by weight of nickel or cobalt and from 0.1 to 5% by weight of ruthenium which has been introduced as a solution of a ruthenium halide on a porous metal oxide support comprising at least 50% by weight of activated aluminum oxide. The catalyst is, for example, used in the form of pellets having a length and a diameter of about 3 mm. It is clearly emphasized in the document that although nonhalides such as ruthenium oxide, ruthenium sulfate, ruthenium nitrate, ruthenium nitrosylnitrate, ruthenium ammonium nitrate, ruthenium acetylacetonate and potassium perruthenate increase the activity of a nickel or cobalt catalyst, they do not give any significant improvement in the selectivity in organic hydrogenations compared to the corresponding catalysts without addition of ruthenium. Journal of Catalysis 161, pages 96 to 106 (1996) describes the use of supported and unsupported ruthenium-cobalt catalysts for hydrogenations, in particular of nitrile compounds. However, the document gives no pointer to the use of catalysts comprising ruthenium and cobalt for the hydrogenative amination of monoethylene glycol by means of ammonia.

EP-A 0 839 575 discloses an amine catalyst comprising, based on the total weight of the catalyst, from greater than 6 to 50% by weight of cobalt, nickel or a mixture thereof, from 0.001 to 25% by weight of ruthenium, from 0 to 10% by weight of copper and from 0 to 5% by weight of promoters on a porous metal oxide support, with the support not being impregnated with halogen compounds. The catalysts do not, in particular, cause corrosion and at the same time have good durability and high selectivity to ethylenediamine in the amination of monoethanolamine by means of ammonia.

In the light of this prior art, it was an object of the invention to provide a process for preparing ethylene amines and ethanolamines by hydrogenative amination of MEG which displays increased selectivity to linear ethylene amines and ethanolamines.

The object is achieved by a process for preparing ethylene amines and ethanolamines by hydrogenative amination of monoethylene glycol and ammonia in the presence of a catalyst, wherein the process is carried out in two process stages in which in the first process stage, the amination is carried out over a hydroamination catalyst to a monoethylene glycol conversion of not more than 40% and in the second process stage, a supported catalyst having an active composition comprising ruthenium and cobalt and no further additional metal of group VII and also no metal of group IB is used in the form of shaped catalyst bodies which in the case of a spherical shape or rod shape in each case have a diameter of <3 mm, in the case of a pellet shape have a height of <3 mm and in the case of all other geometries in each case have an equivalent diameter L=1/a' of <0.70 mm, where a' is the external surface area per unit volume ($mm_s^2/mm_p^3$) and:

$$a' = \frac{Ap}{Vp}$$

where $A_p$ is the external surface area of the shaped catalyst body ($mm_s^2$) and $V_p$ is the volume of the shaped catalyst body ($mm_p^3$), and the second process stage is carried out at a temperature which is at least 10° C. higher than that in the first process stage.

The first process stage is preferably carried out to a monoethylene glycol conversion of not more than 30%.

The surface area and the volume of the shaped catalyst body are obtained from the geometric dimensions of the shaped body according to the known mathematical formulae.

The volume can also be calculated by the following method in which:

1. the internal porosity of the shaped body is determined (e.g. by measurement of the water uptake in [ml/g of cat] at room temperature and a total pressure of 1 bar),
2. the displacement of the shaped body on immersion in a liquid (e.g. by gas displacement by means of a helium pycnometer) is determined and
3. the sum of the two volumes is formed.

The surface area can also be calculated theoretically by the following method in which an envelope which surrounds the shaped body and whose curve radii are not more than 5 ttm (so that the internal pore surface area is not included by "intrusion" of the envelope into the pores) and contacts the shaped body as closely as possible (no intersection with the support) is defined. This would clearly correspond to a very thin film which is placed around the shaped body and is then evacuated from inside so that the film lies as closely as possible around the shaped body.

The MEG used as starting material can be prepared by known methods, for example by reaction of ethylene oxide with water.

The reaction according to the invention in the first process stage is generally carried out at a temperature in the range from 130 to 230° C., preferably from 150 to 170° C., and the reaction in the second process stage is generally carried out at a temperature in the range from 150 to 240° C., preferably from 160 to 190° C., with the temperature in the second process stage always having to be at least 10° C. higher than the temperature in the first process stage. The reaction according to the invention is generally carried out at an absolute pressure in the range 1-250 bar, preferably 100-200 bar, in particular 150-200 bar.

MEG and ammonia are preferably used in a molar ratio in the range from 3 to 30, preferably from 7 to 15, in the first process stage.

The invention is not restricted in respect of the catalysts used in the first process stage; it is possible to use all known hydroamination catalysts, for example catalysts comprising nickel, cobalt and copper as active composition. It is important that the conversion in the first process stage is restricted to not more than 40% of monoethylene glycol, preferably not more than 30%.

This gives a mixture in which MEOA predominates and which is introduced directly, in particular without intermediate removal of ammonia, into the second process stage.

In the second process stage, supported catalysts are generally used in a form which consists only of the catalytically active composition in, if appropriate, a shaping aid, for example graphite or stearic acid, or as supported catalyst, i.e. the catalytically active composition is present on a largely inactive support. When supported catalysts are used, the proportion of the support based on the total mass of the catalyst (active composition plus support) is preferably from 10 to 90% by weight.

As supports, it is possible to use all known suitable supports, for example activated carbon, silicon carbide or metal oxides. The use of metal oxides is preferred. Among metal oxides, preference is given to using aluminum oxide, silicon dioxide, titanium dioxide, zirconium dioxide, cerium dioxide, zinc oxide, magnesium oxide or mixtures thereof which may, if appropriate, be doped with alkali metal oxides and/or alkaline earth metal oxides. Particular preference is given to ty-aluminum oxide, silicon dioxide, zirconium dioxide, cerium dioxide or titanium dioxide or mixtures thereof.

The support γ-aluminum oxide is preferred.

The supports can be used in any form, for example as extrudates (in the form of rods), pellets, tablets, monoliths, woven meshes, knitted meshes or as powder.

The supported catalysts can be prepared by generally known methods, These include, for instance, impregnation of a support with solutions of compounds of the metal components used. Suitable solvents include all customary solvents such as water, methanol, ethanol or acetone, with preference being given to using water. Furthermore, the catalyst can be prepared by coprecipitation or sequential precipitation of the catalyst components, subsequent filtration and washing of the filtercake. The impregnation or precipitation is followed by a drying step (from 50 to 200° C.) and a calcination step (from 200 to 500° C.). The catalysts are then reduced at final temperatures of from 200 to 400° C. and can subsequently be passivated since the reduced metals are pyrophoric. After installation of the catalysts in the synthesis reactor, the catalysts can be reactivated by reduction by means of hydrogen at temperatures of from 100 to 300° C. before the reaction is started.

The catalyst comprises, as active composition, ruthenium and cobalt in elemental form and no further addition metal of group VIII and no metal of group IB.

To prepare the catalyst, it is possible to use compounds of the metals mentioned, preferably oxides but also nitrates, carbonates or acetates. To finish the catalyst before it is used in the hydrogenative amination, the metal compounds are reduced, preferably by treatment with hydrogen. This gives a catalyst which comprises the metals mentioned in elemental, finely divided form. Here, the proportion of ruthenium in the catalyst is preferably from 0.1 to 10% by weight and the proportion of cobalt is preferably from 0.1 to 50% by weight, in each case based on the total weight of the active composition of the catalyst.

To prepare catalysts having the composition mentioned, various methods are possible; they can be obtained, for example, by precipitation processes known to those skilled in the art and preferably by impregnation processes.

Here it is important that the catalyst is used in the form of small shaped catalyst bodies. For the purposes of the present invention, small shaped catalyst bodies are ones which in the case of a spherical or rod shape in each case have a diameter of <3 mm, in the case of a pellet shape have a height of <3 mm and in the case of all other geometries in each case have an equivalent diameter L=1/a' of <0.70 mm, where a' is the external surface area per unit volume ($mm_s^2/mm_p^3$) and:

$$a' = \frac{Ap}{Vp}$$

where $A_p$ is the external surface area of the shaped catalyst body ($mm_s^2$) and $V_p$ is the volume of the shaped catalyst body ($mm_p^3$).

Particular preference is given to shaped catalyst bodies which in the case of a spherical or rod shape in each case have a diameter of <2.5 mm, in the case of a pellet shape have a height of <2.5 mm and in the case of all other geometries in each case have an equivalent diameter L=1/a' of <0.65 mm.

In the process of the invention, the diffusion paths of the reactants and also of the products are made shorter by the small specific dimension of the catalyst particles, The mean residence time of the molecules in the pores and the probability of an undesirable subsequent reaction are reduced by this. As a consequence of the defined residence time, an increased selectivity can be achieved, in particular in the direction of the desired EDA and DETA.

Preference is given to carrying out the first process stage in a first reactor region or a first reactor and the second process stage in a second reactor region or a second reactor. The catalyst is preferably present as a fixed bed in each reactor region or reactor. The first and second process stages can, for example, each be carried out in a separate tube reactor or shell-and-tube reactor or else in a region of a tube reactor or shell-and-tube reactor, preferably in each case in a single pass.

The catalyst bed is preferably surrounded by an inert material both at the inlet and the outlet of the reactor. As inert material, it is possible to use, for example, Pall rings, spheres of an inert material (for example ceramic, steatite, aluminum).

The reactor can be operated either in the upflow mode or in the downflow mode. In the case of the preferred downflow mode, a liquid distributor for the reactor feed is preferably used at the inlet of the reactor. If two reactors are used, they can both be operated in the upflow mode or the downflow mode. As an alternative, it is possible to operate the first reactor in the upflow mode and the second reactor in the downflow mode, or vice versa.

The first and second reactor regions are advantageously separated from one another by a bed of inert material which has, in particular a thickness in the range from 20 cm to 200 cm, preferably from 30 to 70 cm, particularly preferably 30 cm.

To maintain the catalyst activity, 0.01-2.00% by weight, particularly preferably 0.20-0.60% by weight, of hydrogen (based on the reactor feed MEG+$NH_3$) are preferably fed into the reactor.

In the preferred continuous operation, a selectivity for MEOA of from 10% to 50% and for the total of EDA and DETA of from 30% to 90% is achieved at a WHSV (weight hourly space velocity) over the catalyst of 0.05-1.25 kg/kg*h, preferably 0.1-0.4 kg/kg*h (kg of MEG per kg of cat, per hour) in the conversion range 40-50%, based on MEG.

Further products obtained in the process of the invention are small amounts of diethanolamine, DEOA (SDEOA generally 0-5% by weight), triethanolamine, TEOA ($S_{TEOA}$ generally 0-2% by weight) and higher amines ($S_{higher\ amines}$ generally 2-12% by weight).

The crude reaction products of the process of the invention generally comprise only small amounts of cyclic amines as reaction products (generally in amounts of <20% by weight, in particular <15% by weight, very particularly preferably from 6 to 12% by weight).

The crude reaction products of the process of the invention generally comprise only small amounts of tertiary amines as reaction by-products (generally in amounts of <10% by weight, in particular <7% by weight, very particularly preferably from 0 to 4% by weight). The work-up of the product streams obtained in the process of the invention, which comprise mostly the particularly desired EDA and DETA and also aminoethylethanolamine (AEEA), triethylenetetramine (TETA), piperazine (PIP), N-(2-aminoethyl)piperazine (AEPIP), MEOA and unreacted MEG, can be carried out by distillation methods known to those skilled in the art. (Cf., for example, PEP Report No. 138, "Alkyl Amines", SRI International, 0311981, pages 81-99, 117, and DE-A-10349059 (BASF AG)).

The distillation columns required for the recovery of the individual products, especially the particularly desired EDA and DETA, in pure form by distillation can be designed by a person skilled in the art using methods with which he will be familiar (e.g. number of theoretical plates, reflux ratio, etc.).

The reaction product mixture resulting from the reaction is particularly preferably fractionated by multistage distillation.

For example, the fractionation of the reaction product mixture resulting from the reaction is carried out in two separation sequences by multistage distillation, with ammonia and any hydrogen present firstly being separated off in the first separation sequence and separation into unreacted MEG and MEOA, EDA, PIP, DETA, AEEA, AEPIP, TETA and higher ethylene amines being effected in the second separation sequence.

Ammonia obtained in the fractionation of the reaction product mixture resulting from the reaction is preferably recirculated to the reaction.

The amination can preferably be carried out in the presence of water; the addition of water leads to better selectivities for MEOA.

Monoethanolamine from the product mixture from the hydrogenative amination of monoethylene glycol can advantageously be recycled to the reaction, in particular to the second reactor region or the second reactor.

The invention is illustrated below with the aid of an example:

83 g of a standard catalyst in the form of 5×3 mm pellets comprising, in each case in percent by weight: nickel oxide 49.5, copper oxide 16.5, zirconium dioxide 29.5, molybdenum oxide 1.5 and graphite 3 were introduced into a first reactor and 30 g of a catalyst prepared as described below were introduced into a second reactor connected in series with the first:

151 g of $Al_2O_3$ extrudates having a diameter of 1.5 mm were allowed to stand with 128 ml of an aqueous impregnation solution comprising 148 g of Ru nitrosyl nitrate and 46.5 g of cobalt nitrate hexahydrate at room temperature for 60 minutes with repeated good mixing. The extrudates were subsequently dried at 120° C. for 4 hours without being agitated and calcined at 600° C. under 150 l/h of air for 2 hours. The catalyst comprised 4.1% by weight of metallic cobalt and 7.1% by weight of metallic ruthenium, in each case based on the total weight of the catalyst.

After activation by means of hydrogen, 14.8 g/h of MEG, 42.4 g/h of ammonia and 14.6 standard l/h of hydrogen were fed in continuously to the first reactor at a pressure of 200 bar absolute. The temperature in the first reactor was set isothermally to 150° C., and that in the second reactor was set to 170° C. The MEG conversion determined by gas chromatography was 42.6%, with the proportions of the components EDA, MEOA, DEOA, PIP, DETA and AEEA which are reported in the following table being obtained.

diameter of less than 3 mm when it is spherical or rod-shaped, a height of less than 3 mm when it is pellet-shaped, and an equivalent diameter L=1/a' of less than 0.70 mm when it is any other geometry, wherein a' is the external surface area per unit volume ($mm_s^2/mm_p^3$):

$$a' = \frac{A_p}{V_p}$$

wherein $A_p$ is the external surface area of the shaped catalyst body ($mm_s^3$) and $V_p$ is the volume of the shaped catalyst body ($mm_p^3$), with the proviso that said active composition comprises no further metal of group VIII and no metal of group IB.

2. The process of claim 1, wherein, in said first process stage, said amination results in a monoethylene glycol conversion of not more than 30%.

3. The process of claim 1, wherein said supported catalyst comprises a proportion of from 0.1 to 10% by weight of ruthenium and a proportion of from 0.1 to 50% by weight of cobalt, in each case based on the total weight of said supported catalyst.

4. The process of claim 1, wherein the catalyst support for said supported catalyst comprises γ-aluminum oxide.

5. The process of claim 1, wherein said shaped catalyst body has a diameter of less than 2.5 mm when it is spherical or rod-shaped, a height of less than 2.5 mm when it is pellet-shaped, and an equivalent diameter L=1/a' of less than 0.65 mm when it is any other geometry.

6. The process of claim 1, wherein said first process stage is carried out in a first reactor region or a first reactor and said second process stage is carried out in a second reactor region or a second reactor.

7. The process of claim 6, wherein said first reactor region and said second reactor region are separated from one another by a bed of inert material.

8. The process of claim 7, wherein the thickness of said bed of inert material is in the range of from 20 cm to 200 cm.

| Example | Temperature (° C.) | Pressure (bar) | H₂ (mol of H₂/mol of MEG) | WHSV (kg/l*h) | Molar ratio (NH₃/MEG) | Conversion of MEG % |
|---------|---|---|---|---|---|---|
| | 150*-170** | 200 | 0.6 | 0.10 | 15 | 42.6 |

| Example | EDA % | MEOA % | PIP % | DETA % | AEEA % | DEOA % | Balance % | EDA/PIP |
|---------|---|---|---|---|---|---|---|---|
| | 49.5 | 29.0 | 6.8 | 3.9 | 5.7 | 1.7 | 3.4 | 7.3 |

*in the 1st process stage
**in the 2nd process stage

The invention claimed is:

1. A process for preparing ethylene amines and ethanolamines comprising hydrogenatively aminating monoethylene glycol and ammonia in the presence of a catalyst, wherein said process comprises a first and a second process stage, wherein:
   in said first process stage, said amination is carried out over a hydroamination catalyst resulting in monoethylene glycol conversion of not more than 40%; and
   in said second process stage, a supported catalyst which comprises an active composition comprising ruthenium and cobalt and is in the form of a shaped catalyst body is employed, wherein said shaped catalyst body has a 9. The process of claim 1, wherein monoethanolamine from the product mixture of the hydrogenative amination of mono ethylene glycol is recycled to the reaction.

10. The process of claim 9, wherein said process forms a product mixture comprising monoethanolamine and said monoethanolamine is recycled to said second reactor region or to said second reactor.

11. The process of claim 8, wherein the thickness of said bed of inert material is in the range of from 30 cm to 70 cm.

12. The process of claim 8, wherein the thickness of said bed of inert material is 30 cm.

* * * * *